United States Patent [19]
Munro

[11] Patent Number: 5,957,849
[45] Date of Patent: Sep. 28, 1999

[54] ENDOLUMINAL ULTRASOUND-GUIDED RESECTOSCOPE

[75] Inventor: Malcolm G. Munro, Sherman Oaks, Calif.

[73] Assignee: The Regents of the University of California, Oakland, Calif.

[21] Appl. No.: 08/884,980

[22] Filed: Jun. 30, 1997

[51] Int. Cl.[6] .................................................. A61B 8/00
[52] U.S. Cl. ........................... 600/459; 600/463; 600/462
[58] Field of Search .................................... 600/463, 464, 600/462, 459, 460, 461

[56] References Cited

U.S. PATENT DOCUMENTS

| | | | |
|---|---|---|---|
| 5,190,046 | 3/1993 | Sturman ................................. | 600/463 |
| 5,275,166 | 1/1994 | Vaitekunas et al. . | |
| 5,383,460 | 1/1995 | Jang et al. ............................... | 600/463 |
| 5,471,988 | 12/1995 | Fujio et al. .............................. | 600/463 |
| 5,485,846 | 1/1996 | Webler et al. ........................... | 600/463 |

OTHER PUBLICATIONS

"Intraoperative Ultrasound Guidance for Intrauterine Endoscopic Surgery", vol. 62, No. 3 of Fertility and Sterility, Sep. 1994, by Letterie, et al., pp. 654–656.

"Intrauterine Ultrasonography with a High–Frequency Probe: Preliminary Report", vol. 85, No. 3, Mar. 1995, by Kikuchi, et al., pp. 457–460.

Primary Examiner—Marvin M. Lateef
Assistant Examiner—Maulin Patel
Attorney, Agent, or Firm—Daniel L. Dawes

[57] ABSTRACT

A surgical implement, such as a surgical electrode, and an ultrasound transducer, both extend through a single elongated insertion member, typically, a catheter. The ultrasound transducer extends from the proximal region of the surgical instrument containing the instrument controls toward the distal end of the catheter from which at least the operative tip of the surgical implement and the ultrasound transducer extend. In one embodiment, the catheter also contains a fiber-optic endoscope, thus allowing visual as well as ultrasound monitoring of the surgical site, before, during and after conduct of the surgical procedures. Means are provided for rotation of the ultrasound transducer to enable generation of a circular tissue reflectivity image transverse to the axis of the ultrasound transducer. Means are also provided for selective longitudinal movement of all elements contained within the catheter. Liquid crystal or other display means are provided to facilitate visual monitoring of the ultrasound and if present the endoscope outputs in real time. In embodiments including an endoscope, an optical eyepiece is provided to facilitate monitoring of its output. An ultrasound medium within the surgical site is provided by fluid inlet and removal means through the catheter.

30 Claims, 4 Drawing Sheets

ENDOLUMINAL ULTRASOUND-GUIDED RESECTOSCOPE

BACKGROUND OF THE INVENTION

1. Field of the Invention

This invention relates to the field of endoscopic surgical instruments and, more particularly, to such instruments whose distal portion, bearing surgical implements, may be inserted through natural bodily orifices or surgical incisions and guided to and at the surgical site by endoluminal and ultrasound means.

2. Description of Prior Art

The scope of surgical techniques which may be performed endoscopically has greatly expanded in recent years. This rapid growth is the result of increasingly sophisticated ultrasound-guided and endoluminal instruments.

Such instruments and the surgical techniques which have developed in response to their availability have resulted from a need to provide surgical treatment with a minimum of discomfort and risk to the patient and with decreased recovery time. Many surgical procedures which, only a dozen years ago, would have entailed a large incision, a significant level of anesthesia, and a lengthy, closely monitored, recovery can now be performed on an outpatient basis with only minor analgesia.

Typical of modern endoscopic surgical techniques are those now commonly applied to gall bladder removal and hernia repair. As generally performed today, such abdominal surgical procedures may entail the creation of only two small incisions. One of these admits the surgical instrument and the other allows access of an endoluminal (usually fiber-optic) viewing instrument, to guide the surgeon to the surgical site and to allow him to monitor the procedure visually, in real time.

However, in Vaitekunas et al, U.S. Pat. No. 5,275,166 it is pointed out that the difficulty in this type of procedure, and, indeed, in all types of endoscopic surgery, is that the surgeon can not tactually contact the area to which he is applying the surgical techniques. Thus, while the area can be visually monitored, in real time, by use of the endoscope, tiny and similar-looking—structures can not readily be distinguished, as they might be if the surgeon could apply his trained sense of touch.

Thus, Vaitekunas describes an earlier patent issued to Silverstein et al—U.S. Pat. No. 4,770,185 in which output from a catheter introduced ultrasound transducer is caused to generate a Doppler signal to produce an audible sound, varying with the instantaneous transducer output. Since the transparency of bodily tissues to ultrasound (i.e., sound generally in the 5–50 MHz range) varies characteristically and quite predictably, the quality and quantity of the sound generated by the Silverstein loudspeaker allows the surgeon to distinguish certain internal tissues and processes in real time, namely here, venous versus arterial blood flow.

However, Vaitekunas points out that the Silverstein procedure necessitates removal of the ultrasound transducer catheter and subsequent insertion of the surgical implement catheter, for performance of the surgical procedure, presumably under the continued guidance of a transdermal ultrasound transducer. Accordingly, Vaitekunas seeks to remedy this situation by combining, in one instrument, the ultrasound transducer of Silverstein and the surgical implement, itself.

With this combination, Vaitekunas describes performance of endoscopic abdominal surgery by means of such a combination instrument, inserted into the abdominal cavity through a first small incision, with visual monitoring provided by an ordinary (presumably, fiber-optic) endoscope. Using the audible signals generated from the ultrasound transducer, the surgeon "feels" the tissues seen by means of the endoscope. Thus, he is less likely to confuse the bile duct with a blood vessel.

Although Vaitekunas' combination of an ultrasound transducer and surgical implement in a single surgical instrument is undeniably a great improvement, there is still the problem of the separate endoscope, which someone must manipulate. The surgeon must either manipulate both instruments himself, or he must continuously direct a skilled assistant to manipulate the endoscope, while he controls the surgical implement. This creates an ongoing, unwanted distraction for the surgeon, who would undoubtedly rather concentrate on the surgical procedure.

Approaching the ultimate problem from another direction, for a moment, it may be instructive to examine other developments and their deficiencies. These developments relate primarily to the field of intrauterine endoscopic surgery.

In modern intrauterine surgery, a surgical instrument contained within a catheter is inserted transcervically into the uterus. Typical of such an instrument is a resectoscope. At the distal end of this device are two projecting apparatus: the surgical implement itself, usually a mono-polar electrode by which the resection is performed; and a fiber-optic endoscope, by which the surgeon visually monitors the procedure. Since the distal end of the endoscope is located precisely adjacent to the tip of the electrode, the surgeon may continuously view the electrode and its activity at the surgical site, and is thus able to perform intricate intrauterine surgical procedures. The fact that a modern resectoscope has an external diameter of only a few millimeters, often less than five millimeters, means that such a procedure may be conducted with an absolute minimum of discomfort to the patient, both in insertion and in the course of movement within the uterus. In fact, some intrauterine surgical procedures may now be conducted, using such a resectoscope, with minimal or no analgesia.

There are potential hazards in the use of a resectoscope. While the surgeon is able to visually monitor the procedure in real time with great precision, this is, after all, only a surface view. If, for example, a small blood vessel lies just below the interior uterine surface in close proximity to the surgical site, the surgeon might not be aware of this unless an accident occurs and the vessel is cut by the electrode. Even more serious is the possibility that in a fairly invasive surgical procedure a uterine puncture, or puncture of the underlying bowel might occur. These events are particularly significant and dangerous, because endoscopic surgery, particularly noninvasive surgery of the general type described, may be and will increasingly be performed an outpatient basis. Thus, in such an occurrence remedial procedures and apparatus might not readily be available, and the patient is exposed to the risk of serious complications.

Recognizing this risk, a number of researchers have investigated the use of ultrasound in support of resectoscopic intrauterine surgery. In a paper entitled "Intraoperative ultrasound guidance for intrauterine endoscopic surgery", published at pages 654–656 of Volume 62, Number 3 of *Fertility and Sterility* (September 1994), the authors, Drs. Gerard S. Letterie and Dawna J. Kramer, describe the positive results of their study of transabdominal ultrasound monitoring of resectoscopic procedures. It should again be pointed out in this context, that we are still referring to remote monitoring of the surgical site, here transabdominally. Still, the surgeon manipulating the resectoscope and visually monitoring the site through the endoscope can only know the approximate location of underlying structures. Not enough precision is provided by this method.

In "Intrauterine Ultrasonography with a High-Frequency Probe: Preliminary Report", Drs. Akihiko Kikuchi, Takashi Okai, Koichi Kobayashi, Masato Sakai, Eiji Ryo and Yuji Taketani report, at pages 457–460 of *Instruments & Methods*, Volume 85, Number 3 (March 1995) report that, by transcervical insertion of an ultrasound transducer probe of 2 millimeters diameter without analgesia they were able to discover and classify a number of uterine anomalies with some precision.

The latter closely resembles the above teachings of Silverstein et al, in that surgery to remove such anomalies would necessitate removal of the ultrasound transducer catheter and subsequent insertion of, presumably an ordinary, modern resectoscope, probably with transabdominal ultrasound monitoring.

What is needed, then, is a surgical instrument which can be controlled entirely by the surgeon himself, which combines the surgical implement, endoscopic monitoring means and an ultrasound transducer, all directed, or directable at the precise surgical site to allow the surgical procedure to proceed, internally, with both surface (optical) and subsurface (ultrasound) real time monitoring. It would be particularly beneficial to provide such an instrument whose distal housing is sufficiently small in diameter to permit insertion through a single, small surgical incision or preferably, which is incorporated within a catheter, so that insertion might be made through a small natural bodily orifice without the need for an incision.

What is also needed is such an improved apparatus which, by use of precise ultrasound monitoring through use of a transducer in close proximity to the distal end of the surgical implement, entirely obviates the need for any optical monitoring at all, whether by incorporated fiberoptic endoscopic means or otherwise.

Finally, what is needed is a surgical instrument which combines a surgical implement with an ultrasound transducer located at or precisely near the operative focus of the surgical implement with or without the addition of a similarly-placed endoscope, which is miniaturized and contained within a catheter of sufficiently small diameter to permit use of the instrument by insertion through a single, small surgical incision or preferably through small natural bodily orifices, such as the cervix or the urinary canal to facilitate noninvasive surgical procedures (e.g., within the uterus, the bladder, the prostate, the cranial sinuses and the ear) with the need for a significantly lesser degree of analgesia.

BRIEF SUMMARY OF THE INVENTION

The present invention comprises a surgical apparatus which combines, in one device, which may be totally manipulated by one hand of the surgeon, a surgical implement together with means allowing the surgeon to accurately monitor the surgical procedure in real time. In the preferred embodiments, such monitoring means includes both an endoscope and an ultrasound transducer. However, in an alternative embodiment, no endoscope is present and all monitoring is accomplished by means of an ultrasound transducer.

In the preferred embodiments, the surgical implement and the monitoring means are miniaturized and housed within a catheter, and depending on the particular embodiment some or all components of the synergistic surgical apparatus may easily be extended or retracted from the distal end of the catheter by the surgeon at will, when the apparatus is inserted and directed at the surgical site.

The invention may now be visualized by turning to the following drawings wherein like elements are referenced by like numerals.

DETAILED DESCRIPTION OF THE PREFERRED EMBODIMENTS

It will be readily noted that the relative proportions of many elements shown in the various Figures are incorrect. This is for the purpose of providing additional clarity in the following discussion by which the practitioner will readily be able to determine the correct proportions of any surgical instrument implemented according to these teachings.

Figures 1, 2:
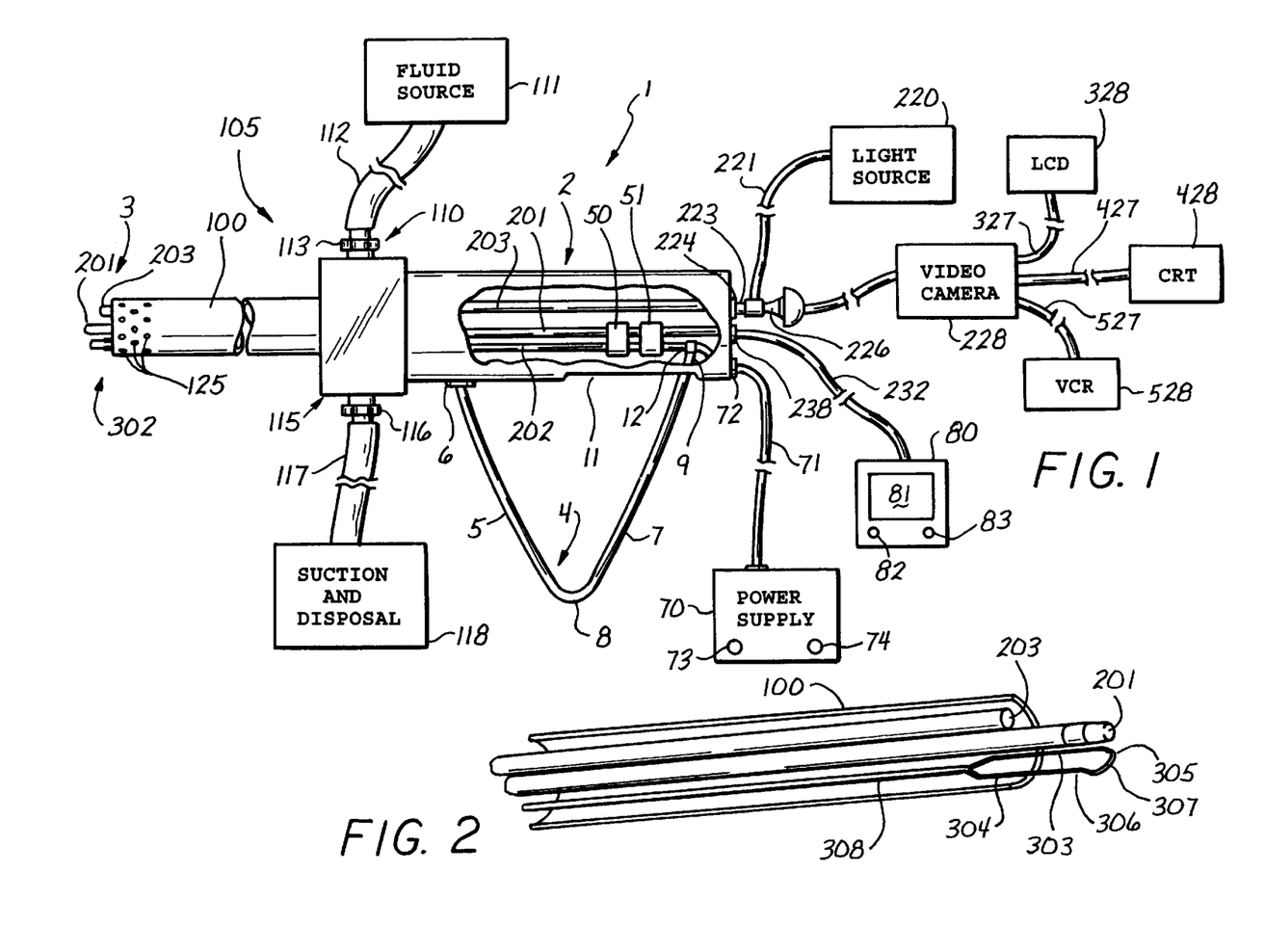
FIG. 1 is a partially cutaway side elevational view of the principal embodiment of the surgical instrument of the present invention, displaying in block diagrammatic form various ancillary apparatus which may be combined with the instrument.
FIG. 2 is an isometric view of the distal end of a surgical electrode.

Referring now to FIG. 1, the surgical instrument of the preferred embodiment will first be described broadly. Surgical instrument 1 comprises a proximal region 2 and a distal end 3. In the principal embodiment of the invention, shown in FIG. 1, proximal region 2 includes an "Iglesas element"

4, which the surgeon grasps. Iglesas element 4 comprises a compressible spring, which is shown in its extended position in FIG. 1. The forward arm 5 of the Iglesas element 4 is secured to a housing 10 by attachment at a fixture 6. A rear arm 7 of the Iglesas element 4 constitutes a compressible spring element, i.e., when the surgeon squeezes Iglesas element 4, rear arm 7 tends to move forward.

While the Iglesas element 4 may be implemented as a rigid forward arm 5, to which the flexible rear arm 7 is secured at their junction 8, it may also consist simply of a V-shaped spring, as shown secured to fixture 6. In any event, at least rear arm 7 is resilient, and a tip 9 of rear arm 7 is thus free to move forward. The latter is true because rear arm 7 is inserted into a longitudinal slot 11 in the lower side of housing 10.

Within housing 10, tip 9 of rear arm 7 of Iglesas element 4 is secured to a rear end 12 of a surgical implement 202. Thus compression of Iglesas element 4 causes surgical implement 202 to slide forward. Surgical element 202 is mounted slideably within housing 10 by means not shown, such means being well within the skill of the ordinary practitioner.

Surgical element 202 continues to extend forward through the housing 10, until its tip 302 emerges from the distal end 3 of the catheter within which it is housed. Thus, compression of Iglesas element 4 ultimately causes tip 302 of surgical implement 202 to extend from distal end 3 of catheter 100, and relaxation of Iglesas element 4 likewise causes tip 302 to retract into catheter 100. In the case of a typical resectoscope, the maximum extent of such movement is in the range of about two centimeters. However, no such limitation of movement is inherent in the invention, and a reasonably skilled practitioner might certainly design an alternative embodiment of the invention within the teachings herein, where a greater or lesser degree of extension is facilitated.

The length of the 11 corresponds to the anticipated maximum extension of the tip 302 of the surgical implement 202 from the catheter 100. In the preferred embodiment of surgical instrument 1, which essentially comprises a resectoscope improved according to the invention, surgical implement 202 is a mono-polar resecting electrode, hereinafter referred to as an "electrode." As shown in FIG. 2, electrode 202 comprises a pair of conducting wires 303, 304 terminating respectively at a first tip 305 and a second tip 306. Between tips 305, 306 is an electrode loop 307. The two wires are carried within an insulated jacket 308 through housing 10 and catheter 100, and are provided with selectively regulated current from a power supply 70 through a supply wire 71 as shown in FIG. 1. The latter extends into housing 10 through a junction 72 to electrode 202 at its rear end 12. Power supply 70 may be a portable generator or, perhaps, an appropriately configured potentiometer device drawing current from a wall socket.

Since such electrodes 202 and their power supplies are well know, no further detail will herein be provided in respect to these elements, except to point out that, in use an arc passes between the distal tips 305, 306 of the electrode 202. It is this arc which performs the resecting function. Initiation and control of the arc can be by various means which in respect to the principal embodiment shown in FIG. 1 is shown generally as a pair of switches 73, 74. Of course other means for initiation and control are possible with switching means incorporated in or on housing 10 or otherwise.

What may principally distinguish the present invention in all embodiments from other surgical instruments disclosed in the art is the addition of an ultrasound transducer extending from distal end 3 of surgical instrument 1. To be sure, ultrasound transducers have been employed to monitor surgical procedures transdermally. As mentioned above, miniaturized ultrasound transducers housed in, and inserted by means of, catheters have been employed for intrauterine inspection, and similar devices having also been employed for intravenous examination.

However, surgical instrument 1 of the present invention employs an ultrasound transducer 201 to precisely guide the surgeon in situ by placement of the transducer 201 in extremely close proximity to the surgical implement 202 itself. Thus, the present invention obviates the need for a separate instrument, which need perhaps be manipulated by another individual or at least by the surgeon's other hand, to accomplish the desired purposes of close ultrasound monitoring during surgical activity. As a result, such monitoring is accomplished with more precision.

As previously suggested, the principle of operation of ultrasound transducers of the type presently contemplated is based on the fact that human tissues demonstrate varying transparency and reflectivity to imposed beams of ultra high frequency sound i.e., of ultrasound, in the general range of about 5–50 MHz. As in many, if not most, ultrasound transducer-based medical devices now commonly in use, ultrasound transducer 201 incorporated into the present surgical instrument 1 is in a state of constant, rapid 360° rotation during use. The "beam" of ultrasound, which radiates outward from the ultrasound transmitter of the transducer 201, thus continuously penetrates a circular region, essentially in a plane transverse to the axis of the transducer. The resulting reflection pattern, received by the transducer microphone is, therefore, a continuous pattern enclosed by a circle, quite analogous to the pattern generated by an ordinary radar device. In the present case, any point within that circle represents a certain quality, namely the relative reflectivity to ultrasound of the fluid medium or a tissue point at that particular radial distance out from the transducer 201 and at that particular angular orientation from a prime radial direction. Each datum received by the microphone identifies the location of the particular point in that circular region in polar coordinates.

For example, if a blood vessel in the tissue surrounding the surgical site lay parallel to the axis of ultrasound transducer 201, and absorption of ultrasound by a blood vessel typically differs from that of surrounding tissues, the scan pattern might reveal a relatively darker or lighter line at a certain radial distance from transducer 201 and at a certain angle from the prime angle in polar coordinates indicative of the diameter of the blood vessel. Thus, by monitoring this pattern, the surgeon will know exactly where the blood vessel is within the tissue surrounding the surgical site, and can thus avoid severing it by keeping surgical implement 202 at a safe distance from it.

Recalling that a complete single scan will yield a pattern corresponding only to a single circular "slice" transverse to the axis of the transducer 201, longitudinal movement of the transducer will generate a collection of such patterns which will define a three-dimensional cylinder of relative reflectivity information coaxial with transducer 201. For this reason it is desirable that the surgeon be able to extend and retract the distal end of ultrasound transducer 201 prior to and during performance of the surgical procedures, so that many such "slices" may be seen. The manner in which this may be accomplished will be discussed below. Miniaturized ultrasound transducers housed in catheters, including various configurations of their constituent transmitters, acoustic lenses and microphones, have been described in the literature, and are commercially available. Accordingly, these elements and their interaction need not be described in further detail.

In intrauterine applications, such a scan can be accomplished without the need to expand the uterus, if a suitable fluid is provided within the normally contracted space, to provide a satisfactory ultrasound transmission medium. The manner in which such fluid may be introduced and circulated will likewise be described below. Obviating the need to expand the uterus can significantly contribute to the overall comfort level of the patient.

Figures 4, 12, 14:
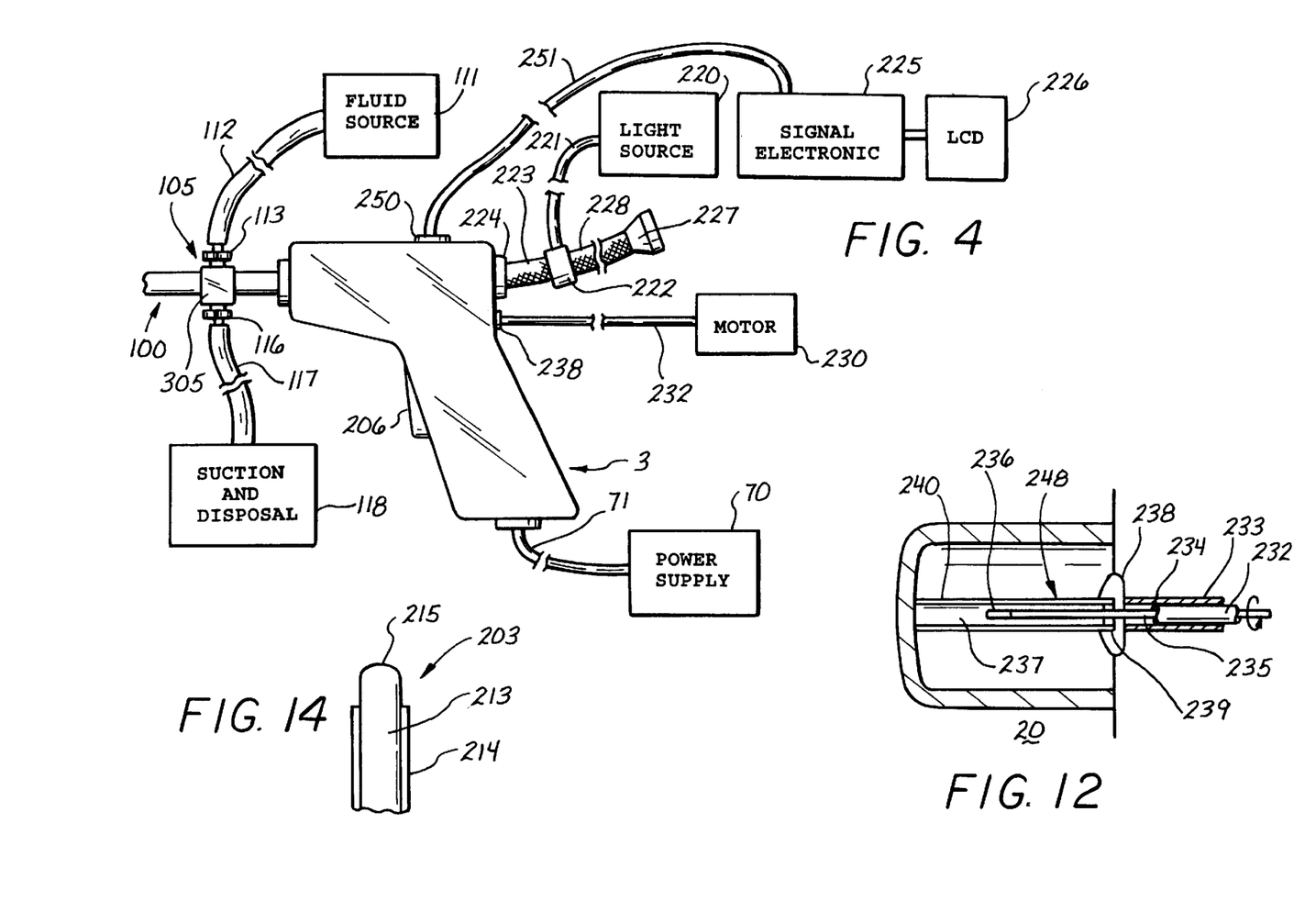
FIG. 4 is a simplified side elevational view of the instrument shown in FIG. 3, displaying, in diagrammatic block form various ancillary apparatus which may be combined with the instrument.
FIG. 12 is a partial cutaway view of the ultrasound transducer rotator.
FIG. 14 is a longitudinal sectional view of the distal end of the fiber-optic endoscope incorporated within the preferred embodiments of the invention.

Having discussed the nature and function of the ultrasound transducer 201 positioned in extremely close proximity to the surgical implement, in the present invention, we will now further examine the operation of ultrasound transducer 201 and its interaction with the other surgical elements in surgical instrument 1. The aforementioned rotation of the ultrasound transducer 201 is induced by means of a conventional transducer cable motor 230, suitably geared to provide the desired rate of rotation. As indicated in FIG. 4, motor 230 may stand alone, or, as indicated in FIG. 1, it may be incorporated into an ultrasound transducer control unit 80, which may also incorporate a viewer 81, e.g., an LCD screen, to permit the surgeon to observe the image generated by ultrasound transducer 201. Activation and regulation of ultrasound control unit 80 is by means of conventional switching devices, shown generally in FIG. 1 as a pair of switches 82, 83. Electrical current to the ultrasound transducer control unit 80 may be provided from the same electrical power supply 70 which provides current to surgical instrument 1, itself, or from another convenient power supply.

Transducer cable motor 230 rotates a transducer input cable 232 at a desired rate of rotation. Referring to FIG. 12, in practice the transducer input cable 232 will be surrounded by a protective, flexible input sheath 233. A tip 234 of transducer input cable 232 is fixed to a rotation transfer rod 235, so that the rotation transfer rod 235 rotates together with the transducer input cable 232.

A transducer drive cable 237 is installed by inserting its tip 248, into an opening 239 in the center of a rotation junction 238, which is sealed into the rear of housing 10 of the surgical instrument. Transducer drive cable 237 is free to rotate within its outer sheath 240. Thus, when tip 248 of transducer drive cable 237 (strictly speaking, tip 248 of its outer sheath 240) is plugged tightly into an opening 239 in rotation junction 238, transducer drive cable sheath 240 is held in place, while rotational force is transferred from rotation transfer rod 235 to transducer drive cable 237, when transfer rod 235 is inserted through the opening in the rotation junction 238 from the opposite (i.e., outer) side into a hollow center 236 of transducer drive cable 237.

The interface between rotation transfer rod 235 and hollow 236 in the center of transducer drive cable 237 must be sufficiently tight so that rotational energy is transferred directly from transducer cable motor 230 to transducer drive cable 237. If the cross sections of rotation transfer rod 235 and of transducer drive cable 237 are both circular, they must be of nearly the same diameter, to insure a tight fit. In that case, hollow 236 in the center of transducer drive cable 237 might be cylindrical, while rotation transfer rod 235 might be slightly frusto-conical. Alternatively, both cross-sections might be square. Having received such rotational force, the entire length of transducer drive cable 237 rotates within its outer sheath 240, responsively rotating the distal end of ultrasound transducer 201 to generate the desired scan.

Figures 3, 5, 6, 11:
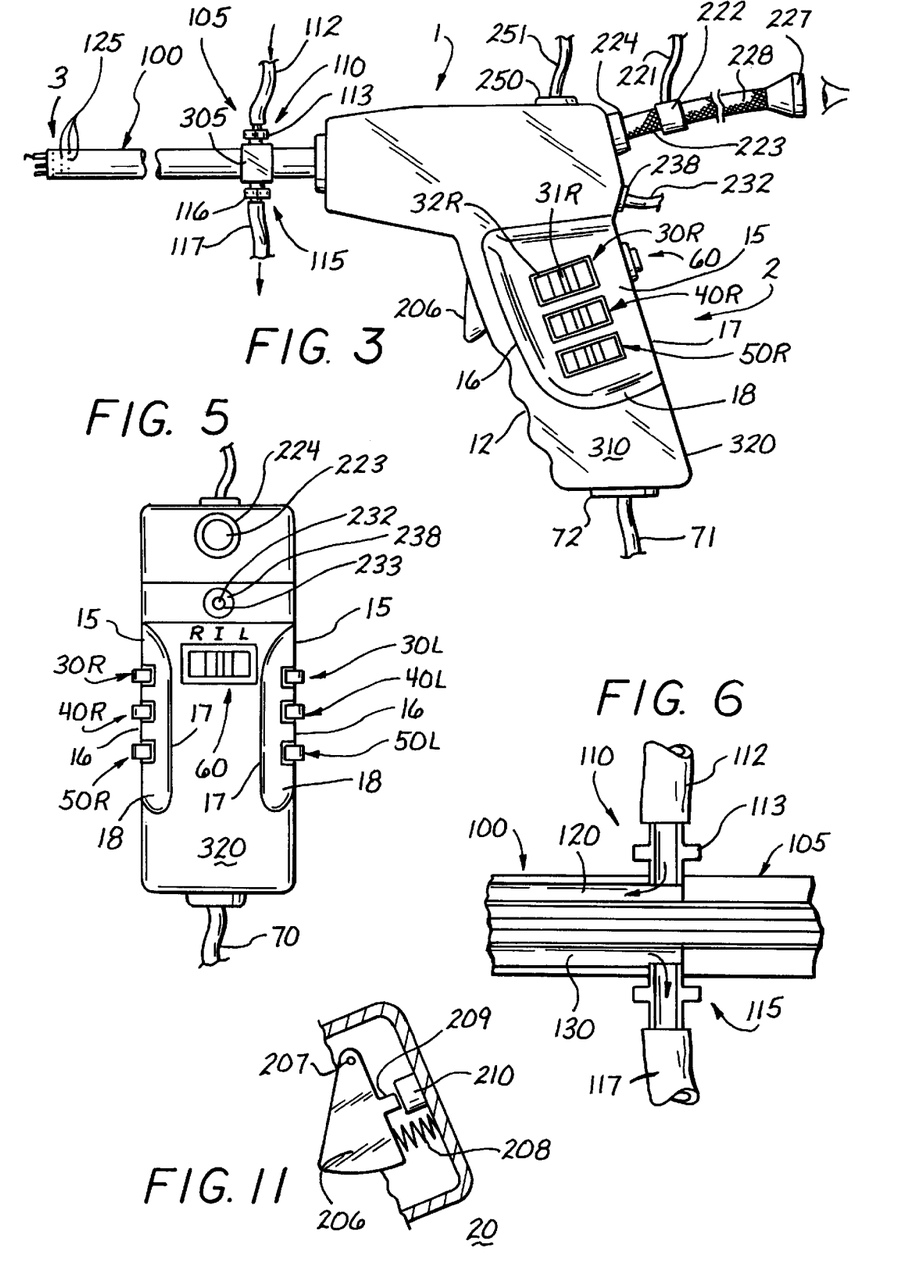
FIG. 3 is a side elevational view of an alternative embodiment of the surgical instrument of the present invention.
FIG. 5 is a rear elevational view of the proximal region of the surgical instrument shown in FIGS. 3 and 4.
FIG. 6 is a cutaway detail view of the fluid inlet and outlet elements of the surgical instrument.
FIG. 11 is a partial cutaway view of the triggering device of the instrument in the alternative embodiment of the surgical instrument shown in FIG. 3.

The output from ultrasound transducer 201, i.e., the analog signal corresponding to a continuous series of instantaneous readings of relative reflectivity, collectively defining the detailed "internal texture" of the entire circular tissue "slice" during an entire circular scan, is fed through a wire (not shown) back through the interior of catheter 100 to signal electronics 225 through an external transducer signal wire 251 as shown in FIG. 4. In the principal embodiment, shown in FIG. 1, these wires are carried in the same housing as the transducer cable itself, and fed directly back to ultrasound transducer control unit 80. Alternatively, as shown in FIGS. 3 and 4, they can be directed through a transducer signal output junction 250 from which external transducer signal wire 251 carries the ultrasound transducer output to the signal electronics element 225

Signal electronics element 225 or other suitable and conventional electronic circuitry converts the continuous analog signal from ultrasound transducer 201 into a form which can be displayed visually. Such display may be made on the same LCD 328 on which the instantaneous optical input from endoscope 203 is displayed, see, below, or, as shown in FIG. 1, it can be displayed on an LCD 81 or other display device incorporated into the ultrasound transducer control unit 80. Alternatively as shown in FIG. 4 it can be displayed on a separate LCD 226, or on another display device. In any case, this is most easily accomplished, in the case of the ultrasound transducer signal, by employing a computer to digitize and store the scan signal from a single "slice", as received, into a data base, and to then convert the data from polar to Cartesian coordinates and feed it serially into the LCD or other scan-generated display as a continuous scan.

While the same LCD 226 or other display device can be used to display both the endoscope signal and the ultrasound transducer signal, possibly by switching between them automatically at some predetermined rate or as selected by the surgeon, it is probably preferable to employ two display devices e.g., LCD's 328, 226 (or 81) which are dedicated to each signal separately. These could be positioned side by side or otherwise as selected by the surgeon. A split screen LCD or CRT could be employed with one portion of the screen, perhaps the left half, displaying the endoscope signal, and another portion, perhaps the right half, displaying the ultrasound transducer signal. The latter method would merely require display of a single perceived side-by-side image, with switching between the two constituent half-screen displays at a higher frequency than the eye can detect. The latter switching and the various computer manipulations required to convert the two signals to LCD, CRT or another type of scan-generated display are well within the skill of an ordinary computer engineer, and commercial devices are available to convert such polar coordinate data for input to such displays. There is, therefore, no need to specify the exact algorithms and their implementation in this discussion, as they play no fundamental role in the invention herein described.

Because an endoscope 203 can only offer the surgeon an optically-derived image of the surface of the surgical site, and because the ultrasound transducer 201 can, by contrast, present an image of an entire axial "slice" of information as to what lies below the surface, it can easily be seen that, in effect, the output from the ultrasound transducer 201 "leads" that of the endoscope 203. In many or perhaps most cases, the surgeon will wish to explore the underlying tissues of the surgical site using the images derived from the ultrasound transducer even before he settles on the precise surgical site, which the endoscope then monitor optically by means of the endoscope, as he initiates and conducts the surgical procedure. Of course, the ultrasound information will also continue to be monitored during surgery. The surgeon will probably not wish to begin until an initial, well-devised ultrasound scan has verified that it is safe to proceed.

Since in the present invention ultrasound transducer 201 is housed in the very same catheter 100 and exposed at its distal end at all times at very nearly the exact location as are the surgical implement 202 and the endoscope 203 in most embodiments, the surgeon may, by viewing the ultrasound image or both the ultrasound and endoscope images, conduct the surgical procedure with extreme precision and with greatly minimized risk of injury to underlying tissues.

Ultrasound transducer 201 extends from within housing 10 and through catheter 100 for ultimate extension beyond distal end 3 of the catheter 100. In the preferred embodiment, shown in FIG. 1, longitudinal movement of the surgical implement 202 by compression of the Iglesas element 4 is generally accompanied by corresponding motion of the ultrasound transducer 201. Thus, those portions of ultrasound transducer 201 and of surgical implement 202 which are within housing 10 are mounted to move together. This may be accomplished by use of one or more oval rings 50, 51 through which the surgical implement 202 or actually its insulating jacket 308 and the ultrasound transducer jacket 240 (see FIG. 12) are passed. To insure that ultrasound transducer 201 and surgical implement 202 move together as a unit during compression and subsequent relaxation of Iglesas element 4, rings 50, 51 must tightly grip both of these devices passing through them.

However, in some applications it may be desired to move ultrasound transducer 201 differentially in respect to surgical implement 202. Here, the grip by rings 50, 51 must be sufficiently tight to cause them to move together when Iglesas element 4 is manipulated, but not so tight as to preclude such relative motion. The latter may be accomplished most easily by manually pushing or pulling transducer input cable 232 into or out of rotation junction 238. Such differential movement might be indicated where the surgeon wishes, for example, to extend the tip of ultrasound transducer 201 beyond tip 302 of electrode 202 to examine the subsurface structures of the region ahead of the latter.

In the preferred embodiments, a third surgical element, the other two being the surgical implement 202 and the ultrasound transducer 201, passes from within housing 10 through catheter 100 and extends from distal end 3 of the latter. As alluded to above, this is endoscope 203, which comprises a fiber-optic cable or some other type of optical conduit now or hereafter known.

It was noted, in the above discussion of pertinent prior art, that a typical resectoscope incorporates a surgical implement, normally, a surgical electrode, as described and a fiberoptic endoscope, both in fixed extension from within the distal end of an insertion catheter. Thus, much of what will be said herein, in this connection except for inclusion of an ultrasound transducer 201 and selective longitudinal movement of the surgical elements, will be quite familiar to surgical gynecologists based on their previous experience.

As shown in FIG. 14, the endoscope, in its simplest aspect, consists of a fiber-optic cable or other optical conduit 213, which may or may not be enclosed in a protective longitudinal sheath 214. Sheath 214 will normally not be necessary, as modem fiber-optic cables suffer little light loss in transmission through their outer peripheries, particularly in a length as short as is anticipated in this context. However, outer sheath 214 might be included as a protective measure.

A distal end 215 of fiber-optic cable 213 is shaped to provide a short focal length, wide angle lens, or a minute wide angle lens may be bonded thereto. In either case, the goal is to allow the surgeon to focus within a circular area at and just beyond the surgical site with some depth of field. Since different applications of the invention will require different focal lengths and conical angles of surveillance, it is left to the practitioner of ordinary skill to determine the actual shape of this distal lens 215 however implemented for the particular application.

It will be obvious that all the surgeon will see by employing this endoscope is the surface of the region being observed, since visible light is the observation medium. But since distal end 215 of endoscope 203 is in very close proximity to distal extremity 302 of electrode 202, use of endoscope 203 will allow him to place and manipulate electrode 202 with great precision, particularly in conjunction with ultrasonic transducer 201 herein described.

Endoscope 203 generates an optical image by projecting light from a light source 220 through an fiber-optic feed cable 221 into the fiber-optic viewing cable 223 as shown in FIG. 4. Merger of these two fiber-optic cables at the beam splitting junction 222 may be accomplished in any convention manner, such as causing fibers of feed cable 221 to be interwoven with those of viewing cable 223, or by use of a prism or a half-silvered mirror. Viewing cable 223 is inserted into surgical instrument 1 at its rear optical junction 224 within which is endoscope fiber-optic cable 213 to which it is optically connected, or which is merely its extension. The light, ultimately from the light source 220, projects through endoscope cable 213 to surgical site is reflected back through the same endoscope cable 213 and back into viewing cable 223, through the beam splitting junction, and through the fiber-optic eyepiece feed cable 226 to an eyepiece 225. Here, the surgeon may view the instantaneous image at the surgical site.

Alternatively, as shown in FIG. 1 the surgeon may wish to view the image on an LCD or CRT screen, or prepare a tape recording of it for later study. Accordingly, in the preferred embodiment of the invention, a CCD 227 is applied to eyepiece 225 as the feed to a video camera 228. The output from video camera 228 is fed to an LCD 328, a CRT 428 and a VCR 528 through leads 327, 427, and 527 respectively. Of course other devices, such as a still camera might receive input from the video camera, and any of the devices mentioned might not be employed. This is entirely a matter of choice for the manufacturer and/or surgeon.

In the preferred embodiment of the invention, shown in FIG. 1, endoscope 203 is fixed, longitudinally, in respect to housing 10 and catheter 100. Its tip 215 can not be extended or retracted in respect to distal end 3 of the catheter 100. In this embodiment, suitable electronics may be provided, in cooperation with distal lens 215 of endoscope 203 to selectively provide a closer or wider angle view of the surgical site. If such electronics are not already incorporated into the video camera 228, they may by a reasonably skilled practitioner be incorporated into the electro-optical line.

Alternatively, in the embodiment of the invention shown in FIG. 3, and described below, means are provided by which endoscope 203 may be selectively extended and retracted in respect to distal end 3 of the catheter 100. Such selective longitudinal movement of endoscope 203 in respect to catheter 100 and other surgical elements 201, 202, is not available in current endoscopic resectoscope.

A rather straightforward means to permit selective longitudinal movement of the endoscope in respect to housing 10 of the principal embodiment of the invention as shown in FIG. 1 would be to implement rear optical junction 224 as a ball bushing within which viewing cable 223 is inserted. Thus, if endoscope 203 is slideably mounted within housing 10, it may be moved longitudinally by merely sliding the viewing cable into and out of rear optical junction 224.

Having now discussed the individual surgical elements of surgical instrument 1 of the present invention, catheter 100 in which they are contained will now be more fully described. Initially, it should be noted that, while the principal intended application of surgical instrument 1 of the present invention is by insertion through relatively small natural bodily orifices, such as the urinary canal or the cervix, the invention is by no means restricted to such applications. Certainly, it is preferable, when possible, to insert this or any other surgical instrument through a natural orifice to obviate the need for and the risk inherent in a surgical incision. There are circumstances where an incision is unavoidable such as in most abdominal cavity surgery. For such and similar applications, the diameter of the elongated housing in which the surgical elements are contained is not as critical as in the case of an application intended for insertion through a natural bodily orifice. Therefore, it should be understood that, in reference to the essential inventive concept herein, the terms "elongated housing" and "catheter" are interchangeable.

Accordingly, while principal emphasis will be placed on a catheter 100 having a diameter of perhaps 2–4 millimeters, the elongated housing can likewise have a significantly larger diameter as generally appears in the Drawing, where such miniaturization is not necessary or even desirable, but where intricate endosurgical procedures are anticipated. It is believed, however, that even in larger diameter applications, surgical instrument 1 of the present invention offers advantages over prior surgical devices, in that performance and close observation of the surgical procedures can by use of the present surgical instrument 1 be accomplished with increased precision, and through no more than a single incision.

Recognizing, then, that reference is equally made to an elongated housing of relatively greater diameter, catheter 100 in the preferred embodiment of the invention is a rigid, elongated tube fabricated of a nontoxic material such as stainless steel. For some applications a flexible catheter 100 might be preferable, and such might be constructed of nylon or a similar material. In a base region 105 of catheter 100 are fluid inlet means 110 and fluid outlet means 115. The essential purpose of these respective means is to provide a flow of appropriate fluid into and out of the surgical site. A constant, steady supply of fluid is necessary for a number of reasons, including cleansing of the surgical site and providing a proper optical and ultrasound medium, as will be discussed further, below. Similarly, the steady outflow of fluid from the surgical site insures removal of resected tissue as well as providing a clean, clear site. Fluid is provided to the fluid inlet means 110 from a fluid source 111 through the fluid inlet tube 112. The latter is secured to surgical instrument 1 by connection to an inlet fitting 113 projecting from a fluid-tight sleeve 305, both of which are entirely conventional and which are constructed of any suitable material, such as nylon or stainless steel.

Similarly, the fluid is removed from the catheter 100 through the fluid outlet means 115 by operation of a conventional suction and disposal apparatus 118, which draws it through the fluid outlet tube 117 joined to the catheter 100 by connection to the outlet fitting 116. Typically, movement of the fluid through the system will be caused solely by a suction and disposal apparatus 118, which pulls the fluid from a fluid source 111. Of course, this could be reversed, and fluid source 111 itself could be pressurized and thus force the fluid through the system and out to a passive disposal station 118. The nature of the fluid depends largely on the nature of surgical implement 202. If surgical implement 202 is a surgical electrode, as shown in the Drawing, the fluid must of course be a nonelectrolyte. If, however, it is a nonelectrical appliance, such as forceps or a ligating clip applicator, the fluid could be ordinary normal saline, distilled water or some other convenient liquid.

Figure 7:
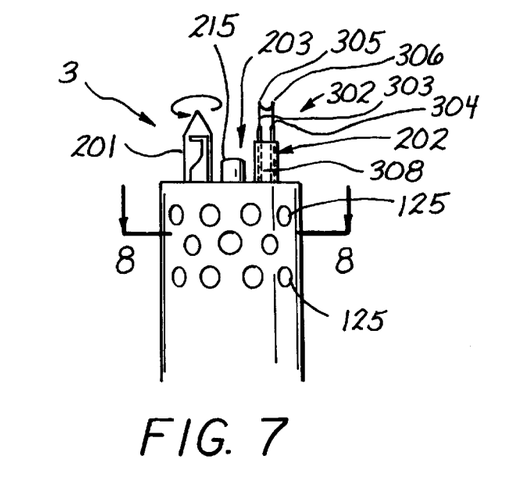
FIG. 7 is a detailed view of the distal end of the of the surgical instrument of the invention.

Referring, now, to FIG. 6, it can be seen that once the fluid enters base region 105 of catheter 100, it flows through an outer fluid inlet channel 120 toward distal end 3 of catheter 100. At distal end 3 of catheter 100, the fluid enters the surgical site by radial expulsion through a group of fluid expulsion orifices 125 shown in FIGS. 7 and 9. Suction then draws the spent fluid back into catheter 100, and thus into an inner fluid outlet channel 130, through which it flows back to base region 105 of the catheter to there be expelled through outlet tube 117.

Figure 8:
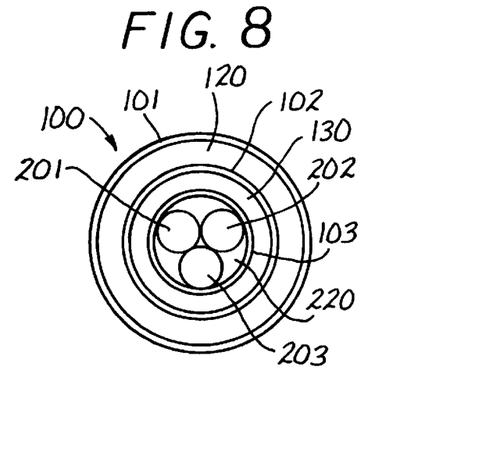
FIG. 8 is a sectional view of the distal end of the surgical instrument according to the principal embodiment as seen through section lines 8—8 in Fig.7.
Figure 10:
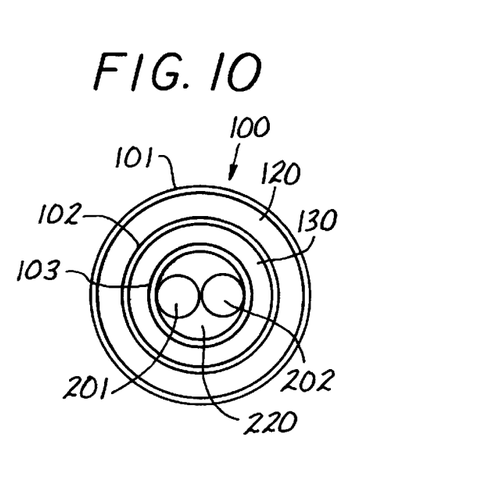
FIG. 10 is a sectional view of the distal end of the instrument according to the alternative embodiment shown in FIG. 9 as seen through section lines 10—10.

FIG. 8 shows the internal structure of distal end 3 of the catheter 100 in a perpendicular cross section of the preferred (three surgical element) embodiments of the invention, and FIG. 10 shows in a perpendicular cross section the internal structure of the distal end 3 of the catheter 100 in the alternative, two surgical element embodiment. Referring to FIG. 8, catheter 100 comprises an outer cylindrical shell 101, a coaxial intermediate cylindrical shell 102 and a coaxial inner cylindrical shell 103. The interstices between outer shell 101 and intermediate shell 102 is a fluid inlet channel 120. The interstices between intermediate shell 102 and inner shell 103 is a fluid outlet channel 130. Surgical elements 201, 202, 203 are carried within inner shell 103, and project outwardly from catheter 100 at its distal end 3. The relative dimensions shown in FIGS. 8 and 10 do not reflect the probable dimensions in the actual apparatus, and are shown in the manner depicted only for clarity. In fact, the space occupied by two fluid channels 120, 130 would in actual catheter 100 likely be less than as shown, relative to that occupied by surgical elements 201, 202, 203, particularly in applications where the overall diameter of the catheter is to be in the order of a few millimeters.

Having now described the principal embodiment of surgical instrument 1 of the present invention, attention will now be drawn to the alternative embodiments, which are principally illustrated in FIGS. 3 and 4. The essential difference between the principal embodiment just described and those now to be described is that in the latter, all surgical elements 201, 202, 203 are longitudinally and mutually extensible and retractable with motive means provided to selectively facilitate such movement. As in the case of the principal embodiment of surgical instrument 1 shown in FIG. 1, the alternative preferred embodiment shown in FIGS. 3 and 4 comprises, in its most general aspect, a proximal region 2 and a distal end 3. In this embodiment, proximal region 2, which the surgeon grasps while performing the surgical procedures, comprises an elongated handle 310, having three finger grip recesses 12, which handle includes a switching panel 15 and a grip 320. A front line 16 of switching panel 15 is at level with the surface of grip 320, but the switching panel smoothly recesses toward a heel recess 17 (see, especially, FIG. 5) at the rear of handle 310. The purpose of this recess is not only to provide a comfortable and secure grip for the surgeon, but primarily to recess the right and left extension switches 30R, 40R, 50R, 30L, 40L, 50L (the letter "R" denoting the extension switches actuatable by the right thumb of a right-handed surgeon, and the letter "L" denoting those actuatable by the left thumb of a left-handed surgeon). Recessing these extension switches also reduces the likelihood that one might accidentally be actuated.

Referring briefly to FIG. 5, it can be seen that a right-left selector switch 60 is provided to allow the surgeon to select which bank of extension switches he wishes to activate depending primarily on his "handedness". The right-left selector switch 60 is actually a three-position switch, the center position inactivating both banks of extension switches, for those periods during which the surgeon wishes not to change the relative distal extension of the various elements, as described below. Referring specifically to the uppermost right extension switch 30R, n activating ridge 31R is pressed forward or rearward by the surgeon, if and as he chooses to distally extend or retract respectively the particular surgical element governed by that switch. The center position (as shown in FIG. 5) is the detent rest position. Pressing activating ridge 31R forward, and sliding it within its slide channel 32R to the "engage" position, activates an extension-retraction motor 130 dedicated to that particular element with positive polarity thus causing distal extension of the particular device for as long as the ridge 31R is pressed forward. Drawing the activating ridge 31R rearward from center likewise causes distal retraction of the same device during the period in which the switch is thus activated.

Figure 13:
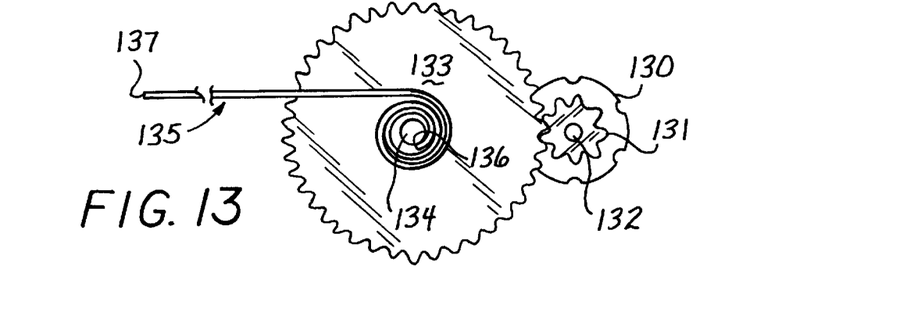
FIG. 13 is a simplified plan view of an extension-retraction motor and associated linkage incorporated within the embodiment shown in FIGS. 3 and 4.

Referring to FIG. 13, a small, dual-polarity motor 130 rotates a drive gear 131 on its shaft 132. Through appropriate and entirely conventional intermediate gearing means for substantial speed reduction, which is shown, for simplicity and convenience in FIG. 13 merely as a single reduction gear 133, motor 130 slowly extends or retracts a flexible extension-retraction cable 135 secured to shaft 134 of reduction gear 133 by means of a pin 136 and wrapped about said shaft in response to positive or negative polarity activation of the motor 130 through the uppermost right switch 30R respectively. Tip 137 of extension-retraction cable 135 is linked to a particular one of the surgical elements of the surgical instrument, by conventional means. Thus, for example, when uppermost right switch 30R is forwardly activated, the component of the surgical instrument, which is directly linked to motor 130 activated by that switch, is distally extended for as long as the switch is activated.

It should be borne in mind that distal movement of none of these surgical elements 201, 202, 203 will normally exceed a centimeter, or perhaps two, because gross movement of entire distal end 3 of surgical instrument 1 may be accomplished by the surgeon merely by moving handle 310, as can likewise be done with the principal embodiment, discussed above. Thus, the only distal movement of these devices likely is merely a fairly small relative movement, e.g., to cause ultrasound transducer 201 (see FIGS. 7 and 9) to project forward or rearward, relatively to surgical implement 202 and/or distal end 215 of endoscope 203. Since the entire diameter of catheter 100 is only of the order of a few millimeters, it can be seen that the scale of distal end 3 of surgical instrument 1 is so fine that no distal extension or retraction of any element is likely to span more than, at most, two centimeters or so. Accordingly, motor 130 can be quite minute, both in size and in output, and a great deal of gear reduction will be required to insure that distal movement is controllably slow and restricted in extent. To insure that the range of distal movement of a particular surgical element remains within predetermined limits, stops can be incorporated in the linkage through extension-retraction cable 135 between the motor and the particular surgical element 201, 202, 203. Again, all mechanical and electrical linkages between uppermost right extension switch 30R and the particular surgical element are entirely conventional, as are motor 130 and that extension switch 30R itself. Their design and implementation are well within the skill of the ordinary practitioner within the teachings herein, and, accordingly need not be further specified or described.

Thus far, mention has been made only of uppermost right extension switch 30R. Of course, the other two right extension switches 40R, 50R on the left side of handle 310, i.e., those operated by a right-handed surgeon for linkage to the other two surgical elements, in the preferred embodiment, and their respective motors and linkages, operate in exactly the same manner. One such switch 30R, 40R, 50R controls distal extension and retraction of a particular surgical element of surgical instrument 1.

Similarly, the left extension switches 30L, 40L, 50L, on the right side of the handle 310, distally extend and retract their respective surgical instrument elements. In particular, extension switch 30L controls the same element as extension switch 30R; extension switch 40L exactly corresponds to extension switch 40R; and extension switch 50L exactly corresponds to extension switch 50R. Which bank of switches is activated is determined by the "handedness" of the surgeon, who merely appropriately engages the right-left selector switch 60. And, as has previously been pointed out, the intermediate position "I" of the right-left selector switch 60 inactivates both banks of these operating switches 30, 40, 50. The manner in which a particular one of three extension switches 30, 40, 50 is dedicated to a particular one of the surgical instrument elements is left entirely to the reasonably skilled practitioner, in light of these teachings. It is anticipated that a manufacturing convention will rapidly be devised, so that all surgical instruments 1 produced according to the present teachings will be consistent in this switch-element dedication, so that all surgeons using these instruments will reflexively operate the proper extension switch, without a moment's hesitation or doubt.

As in the case of the principal embodiment, electrical power is supplied to surgical instrument 1 of this embodiment from a conventional electrical power supply 70, such as a portable generator, through a power cord 71, preferably inserted into a junction 72 at the base of the grip 320. The control and insulated distribution of electrical power through surgical instrument 1 and to its various components is entirely conventional and well within the skill of ordinary practitioners. Since it forms no significant part of the invention, it will not be discussed in detail.

Having now described the overall structure and function of the surgical instrument 1 of the present invention in this alternative embodiment, some further attention will now be drawn to individual surgical elements 201, 202, 203 contained within catheter 100 and projecting from distal end 3 of surgical instrument 1. These are, of course, identical to those which might be incorporated in the principal embodiment shown in FIG. 1 and already discussed hereinabove. Surgical implement 202 itself is the most important of these surgical elements. As in the principal embodiment of the invention, the present embodiment might be viewed as an improved resectoscope primarily intended for intrauterine surgical procedures. Thus, the preferred surgical element is a surgical monopolar electrode 202 of the type previously described.

In the present embodiment, the surgeon selectively activates electrode 202 by depressing a trigger 206, which is mounted within handle 310, and which rotates on its pivot 207. Rotational motion of trigger 206 about its pivot 207 is impeded by a spring 208, which insures that activation will only occur when and to the extent desired. Depression of trigger 206 against the force of spring 208 brings trigger projection 209 into contact with a momentary switch 210 which initiates and sustains the flow of current to surgical electrode 202. Implementation of this switching apparatus and its associated electronics, including the electronics enabling the current from electrical power supply 70 to be controlled for proper generation of the arc at surgical electrode 202, is entirely conventional and well within the skill of the ordinary practitioner, and forms no significant part of the invention disclosed and claimed herein. Indeed, the momentary switch could be replaced by any other convenient switching device, at the able discretion of the ordinary practitioner. Accordingly, these subsidiary elements will not be further described.

As previously pointed out, surgical implement 202, in any embodiment of the invention, might not be a surgical electrode 202, as shown. However, with appropriate and entirely conventional switching means, any of a wide range of surgical implements can be incorporated into surgical instrument 1 of this invention, and selectively activated by depression of trigger 206. It is well within the scope of the present invention to cause the particular surgical implement to be interchangeable with others within surgical instrument 1 merely by detaching it at its base within proximal region 2 of surgical instrument 1, drawing it outward from distal end 3, and reinserting another surgical implement, such as a ligating chip applicator, which is then electronically connected to the same momentary switch 210 for selective activation by depression of trigger 206. This is believed, also, to be well within the skill of the ordinary practitioner of reasonable skill in the relevant art, in light of the present teachings. The surgical implement chosen, whether a surgical electrode 202 or otherwise, will be housed within surgical element channel 220, which is within inner cylindrical shell 103 of catheter 100.

Since the power conduit to surgical implement 202 is merely a flexible wire, distal extension and retraction of the surgical implement 202 is easily accomplished by direct linkage between the particular dedicated motor 130 and surgical implement 202, as activated by the particular extension switch 30, 40, 50. The action will closely resemble extension or retraction of an ordinary automobile radio antenna (except for the probable lack of telescoping, here), when the driver selectively operates a switch at his fingertip. It is recommended that the topmost extension switch 30R, 30L be the one which is dedicated to surgical implement 202, since it is believed that one would naturally expect the top-most switch in the respective bank to operate the most essential element. That or another convention will, in all probability, quickly be adopted to avoid confusion.

Returning momentarily to the issue of distal extension and retraction, it should be noted that fiber-optic cable 213 (or other optical conduit) will normally be very thin and quite flexible. Thus, a small degree of slack may be incorporated in cable 213 or other optical conduit. As is well known, a minor degree and extent of slack will not affect fiber-optic light transmission in any meaningful way. Accordingly, extension-retraction linkage can be placed ahead of i.e., distally from this area of slack. In this manner, when the appropriate linkage is activated by manipulating the particular extension switch 30, 40, 50, endoscope 203 will responsively extend or retract, as desired, and this slack will be correspondingly decreased or increased, respectively, by a slight amount. In any event, it should be borne in mind that such extension and retraction of endoscope 203 will probably be of the order of a few millimeters, and, accordingly, little slack will exist at any time, and little force will be exerted on fiber-optic cable 213 or other optical conduit. Alternatively the ball bushing implementation of the rear optical junction 224 mentioned previously in respect to the principal embodiment shown in FIG. 1 could likewise be incorporated in the embodiment presently under discussion. In this case, no slack would be required, longitudinal movement of endoscope 203 merely causing sliding movement of viewing cable 223 through the rear optical junction 224. Since endoscope 203 will seldom be extended or retracted at all, it is recommended that the extension switches for extension and retraction of the endoscope be the lowermost switches 50R, 50L.

Therefore, both before and during the surgical procedure, as the surgeon continues to endoscopically inspect the surgical site, he may wish to manipulate the relative extension and retraction of ultrasound transducer 201 to see other circular "slices" of data on the nature and condition of nearby underlying tissues. To accomplish this, he need only operate the particular one of the extension switches 30, 40, 50 which is linked to ultrasound transducer 201. This will, in turn, activate the particular motor 130 which is dedicated to that circuit, which will, through mechanical linkage, cause ultrasound transducer 201 to extend or retract as desired. This motion is facilitated by the fact that transducer drive cable 237 is slideably mounted within its outer sheath 240. When, for example, the appropriate extension switch 30, 40, 50 is slid forward, dedicated motor 130 will through mechanical linkage cause transducer drive cable 237 to slide forward within its outer sheath 240 exactly as far as the surgeon wishes. Again, appropriate gear reduction will insure that such movement is slow and precise.

By thus slowly extending the distal end of ultrasound transducer 201 and monitoring the correspondingly changing input displayed on LCD 226 or other display prior to initiation of the surgical procedure, the surgeon will have totally familiarized himself with the underlying "terrain" of the entire surgical site area—prior to commencing surgery. He can, of course, continue to monitor both displays or images during the remainder of the procedure, and can refresh his memory as to the state of all nearby underlying tissues at any time by once again selectively extending and retracting ultrasound transducer 201. This can be done in conjunction with selective extension and retraction of surgical implement 201 and endoscope 203 together or in any combination and to any extent.

Finally, it is important to note that since all three surgical elements 201, 202, 203 are within millimeters of each other and movable separately or in coordinated fashion, a surgeon utilizing surgical instrument 1 of the present invention is not handicapped in this continual monitoring by having mentally to relate a remote ultrasound image with the instantaneous position of surgical implement 201 and the nearby endoscopic image, as has heretofore been necessary.

Figure 9:
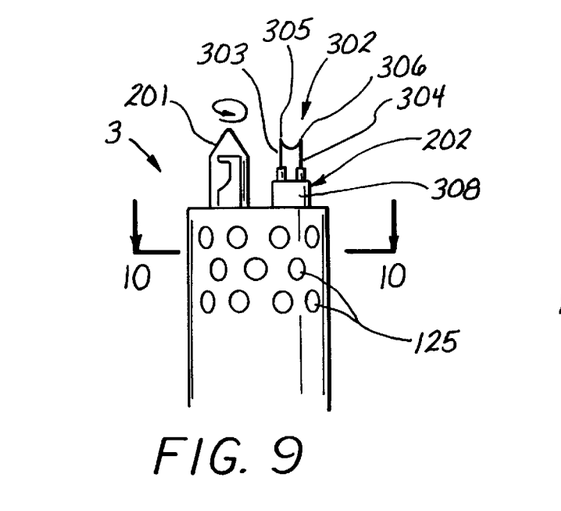
FIG. 9 is a detailed view of the distal end of the surgical instrument according to a two-surgical-element embodiment of the invention.

As shown in FIGS. 9 and 10, an alternative embodiment of the present invention dispenses with endoscope 203 altogether. It is believed that particularly in the case of a surgeon with extensive experience performing surgical procedures in a closely defined portion of the anatomy, e.g., intrauterally, such a surgeon's familiarity with all normal structures within that limited region will allow him to locate and deal with any anomalies merely by monitoring LCD 226 or other display generated from ultrasound transducer 201. This is particularly true in view of the fact that he can, with surgical instrument 1 selectively or continually e.g., by addition of a switch-operated linear oscillator acting on the transducer drive cable 237, extend and retract the distal end of ultrasound transducer 201 as he performs the required surgical procedures. Additionally, as computer imaging techniques continue to progress, the resulting ultrasound-generated display is likely soon to become so precise that it will present a clarity comparable to an endoscopic image but in three dimensions. Accordingly, this alternative embodiment of the present invention, whether in the form shown in FIG. 1 or that shown in FIGS. 3 and 4, dispenses with the endoscope 203, and its associated circuitry and hardware, altogether. In the embodiment shown in FIGS. 3 and 4 in which all three illustrated surgical elements 201, 202, 203 are retained, it is recommended that central extension switch 40R, 40L be dedicated to ultrasound transducer 201, since in all likelihood this element will be extended and retracted in intermediate frequency to that in which surgical implement 202 and endoscope 203 are thus manipulated.

Having now described, in some detail, the construction and operation of surgical instrument 1, it should perhaps again be pointed out that, while the major emphasis has herein been placed on an apparatus in which all three described surgical elements 201, 202, 203 are sufficiently miniaturized for containment within a catheter 100 of a few millimeters diameter for insertion through natural bodily orifices, it is by no means restricted to such applications. Indeed, the fact that this surgical instrument permits precise, continuous monitoring of a surgical site, both visually and ultrasonically at virtually the exact location of the surgical implement 202, itself, offers a far greater breadth of applicability.

For example, in abdominal cavity surgery, such as hernia repair, gall bladder removal or appendectomy to name but a few examples, where heretofore two incisions have been necessary, one for the surgical implement and the other for the endoscope and perhaps a third for an ultrasound transducer, if transabdominal ultrasound monitoring is not employed, using the present invention only a single small incision will suffice to introduce all three surgical elements which can then located and directed at precisely the same surgical site. Not only does such an application offer greater surgical precision, but it also can result in less trauma and risk to the patient and probably a speedier and less eventful recovery.

In addition, while in the foregoing embodiments of the invention, only a single surgical implement 202 projects from distal end 3 of catheter 100 for extension, retraction and operation from switches in the proximal region 2 of surgical instrument 1, the invention is by no means so limited. Indeed, one or more additional surgical implements might be contained within catheter 100. In a suitable modification of the embodiment shown in FIGS. 3 and 4, each switch can be individually activated by selection of a certain position on a conveniently-placed multipositional switch in handle 310 of surgical instrument 1. That position having been selected, switch 210 associated with trigger 206 would then operate that particular implement when the trigger is depressed by the surgeon. Such selection could also responsively cause the specific extension switch 30, 40, 50 which is dedicated to the surgical implement to now provide selective extension and retraction of that particular surgical implement. Of course, by incorporating one or more additional surgical implements, catheter 100 would need to have a somewhat greater diameter. For certain applications e.g., some abdominal cavity procedures, it is believed that availability of additional surgical implements in the same endoscopic and ultrasound-guided surgical instrument would more than offset the slight lack of flexibility inherent in a larger-diameter elongated housing.

Many modifications to basic surgical instrument 1 have been hereinabove described or offered. These modifications are merely suggested as illustrating the fact that many further alternations and modifications may be made by those having ordinary skill in the art without departing from the spirit and scope of the invention. For example, handle 310 and the positions of the various switches and inputs could by an ergonomic engineer of ordinary skill, be modified to securely accommodate a wide range of hand sizes within the scope of the teachings herein.

Therefore, it must be understood that the illustrated and described embodiments have been set forth only for the purpose of example and that these should not be taken as limiting the invention as defined by the claims which follow.

The words used in this Specification to describe the invention and its various embodiments are to be understood not only in the sense of their commonly defined meanings, but also to include, by special definition in this specification, structures, materials or acts beyond the scope of the commonly defined meanings. Thus if an element can be understood in the context of this specification as including more than one meaning, then its use in a claim must be understood ad being generic to all possible meanings supported by the specification and by the word itself.

The definitions of the words or elements of the following claims, therefore, include not only the combination of elements which are literally set forth, but all equivalent structures, materials or acts for performing substantially the same function in substantially the same way to obtain substantially the same result.

Insubstantial departures from the claimed subject matter as viewed by a person with ordinary skill in the art, now known or later devised, are expressly contemplated as being equivalently within the scope of the claims, even though not performing exactly the same function in substantially the same way to obtain substantially the same result. Therefore, substitutions now or later known to one with ordinary skill in the art will be within the scope of the defined elements.

The claims are thus understood to include what is specifically illustrated and described above, what is conceptually equivalent, what can be obviously substituted and also what essentially incorporates the essential idea of the invention.

I claim:

1. A surgical instrument having a proximal region and a distal end, comprising:

an elongated housing extending from said proximal region to said distal end;

a surgical implement within said elongated housing and extending from said elongated housing at said distal end, said surgical implement having an operating theater;

an ultrasound transducer within said elongated housing and extending from said elongated housing at said distal end, said ultrasound transducer comprising:

an ultrasound transmitter extending beyond said distal end for transmitting ultrasound waves into a region extending beyond said operating theater of said surgical implement, and an ultrasound microphone extending beyond said distal end for receiving ultrasound waves reflected from said region extending beyond said operating theater of said surgical implement, said ultrasound transducer generating a signal output responsive to said ultrasound microphone; and a display to visually display said region extending beyond said operating theater of said surgical implement based on said signal output of said ultrasound microphone.

2. The surgical instrument as recited in claim 1, further comprising an ultrasound transducer longitudinal movement control at said proximal region, said ultrasound transducer longitudinal movement control selectively longitudinally moving said ultrasound transducer.

3. The surgical instrument as recited in claim 2, wherein said ultrasound transducer longitudinal movement control comprises a switch having:
    a forward position causing extension of said ultrasound transducer;
    a rear position causing retraction of said ultrasound transducer; and
    a center detent position inactivating longitudinal movement of said ultrasound transducer.

4. The surgical instrument as recited in claim 3, wherein said ultrasound transducer longitudinal movement control comprises a pair of switches each switch in said pair having:
    a forward position causing extension of said ultrasound transducer;
    a rear position causing retraction of said ultrasound transducer; and
    a center detent position inactivating longitudinal movement of said ultrasound transducer; and
    further comprising a right-left selector switch enabling selection of one said switch within said pair or switches.

5. The surgical instrument as recited in claim 1, further comprising surgical implement longitudinal movement control at said proximal region, said surgical implement longitudinal movement control selectively longitudinally moving said surgical implement.

6. The surgical instrument as recited in claim 5, wherein said surgical implement longitudinal movement control comprises a switch having:
    a forward position causing extension of said surgical implement;
    a rear position causing retraction of said surgical implement; and
    a center detent position inactivating longitudinal movement of said surgical implement.

7. The surgical instrument as recited in claim 6, wherein said surgical implement longitudinal movement control comprises a pair of switches each switch in said pair having:
    a forward position causing extension of said surgical implement;
    a rear position causing retraction of said surgical implement; and
    a center detent position inactivating longitudinal movement of said surgical implement; and
    further comprising a right-left selector switch enabling selection of one said switch within said pair or switches.

8. The surgical instrument as recited in claim 1, further comprising an ultrasound transducer rotator for selectively causing rotation of said ultrasound transducer.

9. The surgical instrument as recited in claim 8, wherein:
    said signal output represents a continuous plurality of data, each datum within said plurality comprising information on ultrasound relative reflectivity of a point within said region and the location, in polar coordinates, of said point within said region;
    said display signal represents a continuous plurality of said data in Cartesian coordinates; and
    said display presents a continuous scan of said display signal.

10. The surgical instrument as recited in claim 1, further comprising:
    a fluid inlet to allow fluid to enter said elongated housing and to flow therethrough to said distal end;
    a fluid expulsion port at said distal end to allow fluid from said fluid inlet to be expelled into said region; and
    a fluid collection port to collect fluid from said region and to convey said collected fluid through said elongated member from said distal end.

11. The surgical instrument as recited in claim 10, further comprising a fluid suction causing said collected fluid to be conveyed, by atmospheric pressure, through said elongated member and to be collected therefrom.

12. A surgical instrument having a proximal region and a distal end, comprising:
    an elongated housing extending from said proximal region to said distal end;
    a surgical implement within said elongated housing and extending from said elongated housing at said distal, said surgical implement having a theater of operation;
    an ultrasound transducer within said elongated housing and extending from said elongated housing at said distal end, said ultrasound transducer comprising:
        an ultrasound transmitter extending beyond said distal end for transmitting ultrasound waves into a region extending beyond said theater of operation of said surgical instrument; and
        an ultrasound microphone extending beyond said distal end for receiving ultrasound waves reflected from said region, said ultrasound transducer generating a signal output responsive to said ultrasound microphone;
    a first display for visually presenting a display representative of said signal output depicting said region extending beyond said theater of operation of said surgical instrument;
    an endoscope within said elongated housing, said endoscope having a distal extremity extending from said elongated housing at said distal end, and generating an output comprising reflection of visible light from said region; and
    a monitor to view said output from said endoscope.

13. The surgical implement as recited in claim 12, further comprising:
    second display for visually presenting a display representative of said output generated by said endoscope.

14. The surgical implement as recited in claim 12, wherein said distal extremity of said endoscope comprises an optical lens.

15. The surgical instrument as recited in claim 12, further comprising an ultrasound transducer longitudinal movement control at said proximal region, said ultrasound transducer longitudinal movement control selectively longitudinally moving said ultrasound transducer.

16. The surgical instrument as recited in claim 15, wherein said ultrasound transducer longitudinal movement control comprises a switch having:
    a forward position causing extension of said ultrasound transducer;

a rear position causing retraction of said ultrasound transducer; and a center detent position inactivating longitudinal movement of said ultrasound transducer.

17. The surgical instrument as recited in claim 16, wherein said ultrasound transducer longitudinal movement control comprises a pair of switches, each switch in said pair having:

a forward position causing extension of said ultrasound transducer;

a rear position causing retraction of said ultrasound transducer; and a center detent position inactivating longitudinal movement of said ultrasound transducer; and further comprising a right-left selector switch enabling selection of one said switch within said pair or switches.

18. The surgical instrument as recited in claim 12, further comprising a surgical implement longitudinal movement control at said proximal region, said surgical implement longitudinal movement control selectively longitudinally moving said surgical implement.

19. The surgical instrument as recited in claim 18, wherein said surgical implement longitudinal movement control comprises a switch having:

a forward position causing extension of said surgical implement;

a rear position causing retraction of said surgical implement; and a center detent position inactivating longitudinal movement of said surgical implement.

20. The surgical instrument as recited in claim 19, wherein said surgical implement longitudinal movement control comprises a pair of switches each switch in said pair having:

a forward position causing extension of said surgical implement;

a rear position causing retraction of said surgical implement; and a center detent position inactivating longitudinal movement of said surgical implement; and further comprising a right-left selector switch enabling selection of one said switch within said pair or switches.

21. The surgical instrument as recited in claim 12, further comprising an endoscope longitudinal movement control at said proximal region, said endoscope longitudinal movement control selectively longitudinally moving said endoscope.

22. The surgical instrument as recited in claim 21, wherein said endoscope longitudinal movement control comprises a switch having:

a forward position causing extension of said endoscope;

a rear position causing retraction of said endoscope; and a center detent position inactivating longitudinal movement of said endoscope.

23. The surgical instrument as recited in claim 22, wherein said endoscope longitudinal movement control comprises a pair of switches each switch in said pair having:

a forward position causing extension of said endoscope;

a rear position causing retraction of said endoscope; and a center detent position inactivating longitudinal movement of said endoscope; and further comprising a right-left selector switch enabling selection of one said switch within said pair or switches.

24. The surgical instrument as recited in claim 12, further comprising an ultrasound transducer rotator for selectively causing rotation of said ultrasound transducer.

25. The surgical instrument as recited in claim 24, wherein:

said signal output represents a continuous plurality of data, each datum comprising information on ultrasound relative reflectivity of a point within said region and the location, in polar coordinates, of said point within said region;

said display signal represents a continuous plurality of said data in Cartesian coordinates; and said display presents a continuous scan of said display signal.

26. The surgical instrument as recited in claim 12, further comprising:

a fluid inlet to allow fluid to enter said elongated housing and to flow therethrough to said distal end;

a fluid expulsion port at said distal end to allow fluid from said fluid inlet to be expelled into said region; and a fluid collection port to collect fluid from said region and to convey said collected fluid through said elongated member from said distal end.

27. The surgical instrument as recited in claim 26, wherein said endoscope comprises a fiber-optic endoscope.

28. A surgical instrument having a proximal region and a distal end, comprising:

surgical implement control in said proximal region;

a catheter extending from said proximal region to said distal end, the diameter of said catheter at said distal end not exceeding five millimeters;

a surgical implement within said catheter and extending from said catheter at said distal end, wherein said surgical implement control selectively activates said surgical implement within a theater of operation;

an ultrasound transducer within said catheter and extending from said catheter at said distal end, said ultrasound transducer comprising:

an ultrasound transmitter extending beyond said distal end for transmitting ultrasound waves into a region, and an ultrasound microphone extending beyond said distal end for receiving ultrasound waves reflected from said region, said ultrasound transducer generating a signal output responsive to said ultrasound microphone; and a display for visually presenting a display representative of said signal output.

29. The surgical instrument as recited in claim 28, further comprising:

a fiber-optic endoscope within said catheter, said endoscope having a distal extremity extending from said catheter at said distal end, and generating an output comprising reflection of visible light from said region; and a monitor to view the output from said endoscope.

30. The surgical instrument as recited in claim 29, further comprising:

a fluid inlet to allow fluid to enter said catheter and to flow therethrough to said distal end;

a fluid expulsion port at said distal end to allow fluid from said fluid inlet to be expelled into said region; and a fluid collection port to collect fluid from said region and adapted to convey said collected fluid through said catheter from said distal end.

* * * * *